United States Patent [19]

Rapoport

[11] Patent Number: 4,705,881

[45] Date of Patent: Nov. 10, 1987

[54] CONTINUOUS HYDROCYANATION PROCESS USING ZINC HALIDE PROMOTER

[75] Inventor: Morris Rapoport, Orange, Tex.

[73] Assignee: E. I. Du Pont de Nemours and Company, Wilmington, Del.

[21] Appl. No.: 930,940

[22] Filed: Nov. 17, 1986

[51] Int. Cl.$^4$ .......................................... C07C 120/02
[52] U.S. Cl. .................................................... 558/338
[58] Field of Search ........................................ 558/338

[56] References Cited

U.S. PATENT DOCUMENTS

| | | |
|---|---|---|
| 3,496,217 | 2/1970 | Drinkard, Jr. et al. .............. 558/338 |
| 3,564,040 | 2/1971 | Downing et al. .................... 558/338 |
| 3,766,241 | 10/1973 | Drinkard, Jr. et al. ............. 558/338 |
| 3,903,120 | 9/1975 | Shook, Jr. et al. ............. 558/338 X |
| 4,371,474 | 2/1983 | Rapoport ............................ 558/338 |
| 4,539,302 | 9/1985 | Leyendecker et al. ......... 558/338 X |

*Primary Examiner*—Joseph Paul Brust

[57] ABSTRACT

Process for production of dinitriles using zero-valent nickel catalysts having low ligand ratio, and low amounts of zinc halide as the promoter.

4 Claims, No Drawings

CONTINUOUS HYDROCYANATION PROCESS USING ZINC HALIDE PROMOTER

FIELD OF THE INVENTION

This invention relates to a continuous process for the hydrocyanation of non-conjugated, ethylenically unsaturated organic nitriles to produce the corresponding dinitrile.

BACKGROUND OF PRIOR ART

Processes for the hydrocyanation of ethylenically unsaturated organic nitriles to produce the corresponding dinitrile are known. Drinkard et al. U.S. Pat. No.3,496,217 discloses such a process in which the catalyst employed is a zero-valent nickel compound, and the catalyst is promoted by zinc chloride. Downing et al. U.S. Pat. No.3,564,040 discloses a continuous process for the preparation of dinitrile by hydrocyanation using zero-valent nickel catalyst promoted with high amounts of zinc chloride. Rapoport U.S. Pat. No. 4,371,474 discloses a continuous process for carrying out the hydrocyanation reaction using an arylborane as the catalyst promoter.

SUMMARY OF THE INVENTION

The present invention is an improvement over Drinkard et al. U.S. Pat. No. 3,496,217, and Downing et al. U.S. Pat. No. 3,564,040. In the present invention the hydrocyanation reaction is carried out continuously; the catalyst employed has a low ratio of total ligand to zero-valent nickel, and the amount of zinc chloride promoter employed is low. The process thus produces the desired dinitrile product in satisfactory yields using low amounts of promoter and low amounts of ligand. The invention may be summarized as follows:

This invention is a continuous process for the hydrocyanation of non-conjugated, ethylenically unsaturated organic nitriles having 4 to 20 carbon atoms to produce the corresponding dinitriles which process comprises conducting the hydrocyanation in the presence of a zero-valent nickel ligand-containing catalyst having the general formula $NiL_4$ where L is $P(OAr)_3$ and Ar is an aryl or substituted aryl group having up to 18 carbon atoms promoted with zinc halide, maintaining the temperature of the hydrocyanation at less than about 75° C., controlling the amount of hydrogen cyanide relative to other compounds participating in the reaction such that the overall feed mol ratio of hydrogen cyanide to unsaturated nitrile is in the range of about 0.35/1 to 0.8/1, the overall feed mol ratio of hydrogen cyanide to zero-valent nickel catalyst in the range of about 10/1 to 116/1 and the overall feed mol ratio of hydrogen cyanide to promoter in the range about 30/1 to 800/1 and the molar ratio of total ligand to zero-valent nickel introduced as a catalyst in the range of about 5.4 to 8.2.

Preferably in the continuous process of this invention the organic nitrile starting material is 3- and/or 4-pentenenitrile, the zero-valent nickel catalyst has ligands of tritolylphosphite, and the promoter is zinc chloride.

DETAILED DESCRIPTION OF THE INVENTION

As pointed out in U.S. Pat. No. 4,371,474 by the use of certain organoborane promoters it is possible to carry out the desired hydrocyanation reaction using relatively low ratios of ligand to zero-valent nickel, i.e., ratios of about 5.0 to 7.8. Such relatively low ratios are economically attractive because the ligand recovery and ligand recycle aspects of the process are reduced in size.

In the commercial application of pentenenitrile hydrocyanation using the promoter zinc chloride there are safety and other downstream problems associated with the high concentrations of zinc chloride that build up in the refining system when unreacted pentenenitriles are recovered and the adiponitrile is separated from the other dinitriles. Drinkard in U.S. Pat. No. 3,766,241 addresses these problems by using anhydrous ammonia to precipitate the soluble zinc chloride as the insoluble zinc chloride ammonia complex which can then be removed by filtration or centrifugation prior to refining operations. It is claimed that ammonia treatment reduces corrosiveness, reduces decomposition during distillation, reduces complexing by adiponitrile and other nitriles and improves the yield by 1 to 3%. The present invention has benefits in less ammonia consumption, less waste disposal costs, less pentenenitriles and dinitriles lost in filter cakes or slurries and less cleaning costs.

The present invention allows the production of the desired dinitrile when the ratio of hydrogen cyanide to promoter is in the range of about 30/1 to 800/1, while in the organoborane system described in U.S. Pat. No. 4,371,474 the ratio is in the range of about 30/1 to 400/1.

The present invention can be employed to produce a variety of dinitriles but adiponitrile (ADN) is of particular interest because it is an intermediate used in the production of hexamethylenediamine which in turn is used to produce polyhexamethyleneadipamide, a commercial polyamide useful in forming fibers, films and molded articles.

All ratios referred to herein are molar ratios and the amount of ligand is total ligand unless otherwise specified.

Although the hydrocyanation reaction can employ any non-conjugated, ethylenically unsaturated organic nitrile of from 4 to 20 carbon atoms it is of particular interest in the hydrocyanation of pentenenitriles, e.g., cis- and trans-3-pentenenitrile (3PN), 4-pentenenitrile (4PN) and mixtures thereof (3,4-PN's).

The preparation of zero-valent nickel [Ni(0)]catalyst which is used in the practice of the present invention is found in U.S. Pat. No. 3,903,120 issued on Sept. 1, 1975. Of particular interest is catalyst having the general formula $NiL_4$ where L is a neutral ligand such as a triarylphosphite of the formula $P(OAr)_3$ wherein Ar is an aryl group of up to 18 carbon atoms. Illustrative of the aryl groups are methoxyphenyl, tolyl, xylyl and phenyl Meta- and para-tolyl and mixtures thereof are the preferred aryl groups.

The promoters used in the present invention are zinc halides. Zinc chloride is the preferred zinc halide.

The hydrocyanation can be conducted in one or more steps or stages. If a plurality of stages is employed, it is preferred that the stages be in series with the product from one stage being directed to a subsequent stage. The hydrogen cyanide can be introduced into the first stage or split between stages.

The hydrocyanation must be conducted within certain limits to permit effective use of the zero-valent nickel catalyst with the amount of ligand within the ranges discussed. One limitation is temperature. In order to produce ADN in an acceptable yield at commercially feasible rates the temperature is maintained above 25° C. but less than about 75° C. because at temperatures above 75° C., e.g., 100° C., it has been found that the yield loss is excessive and that no commercially practical adjustments in the reactants or other reaction variables can be made to duplicate performance at lower temperatures. It is preferred to maintain the temperature in the range of 30°-65° C.

Another limitation is in the amount of HCN relative to the other compounds participating in the reaction. As the amount of HCN relative to the 3PN and/or 4PN is increased the conversion of those nitriles increases and their concentration in the reaction products decreases. This results in reduced yield loss. However, the amount of promoter and/or catalyst required to sustain the reaction concurrently increases which adversely affects the economics of the process. Conversely, as the amount of HCN relative to the 3PN and/or 4PN decreases the yield loss increases and the cost of recovering 3PN and/or 4PN increases. By maintaining the ratio of HCN to 3PN and/or 4PN in the range of about 0.35 to 0.8 the benefit of improved yield and the detriment of promoter cost and catalyst and 3,4-PN's recovery costs are balanced.

As the ratio of HCN to Ni(0) increases beyond 116/1 the reaction is difficult to sustain unless excessive amounts of promoter are used. Otherwise, higher temperatures are required and the yield loss increases. At ratios below 10/1 even though the reaction is vigorous and the yield loss is small, the cost of recovering the catalyst becomes excessive. The preferred balance is realized at an HCN/Ni(0) ratio in the range 10/1 to 75/1.

The amount of HCN relative to promoter, e.g., zinc halide in the reaction has been found to affect the activity of the catalyst. When the ratio of HCN/promoter exceeds 800/1 the activity of the catalyst decreases to an extent that the temperature of the reaction must be increased beyond that required to obtain an acceptable yield and unless excessive amounts of catalyst are used the yield loss to 2PN is excessive. When the ratio of HCN/promoter decreases below about 30/1 the cost of promoter is excessive. Operations at a ratio of HCN to promoter within the range of about 30/1 to 800/1 permits operation at an acceptable rate and temperature.

The advantages of using a catalyst having a ligand to nickel ratio of 5.4 to 8.2 are realized when the above variables are maintained as discussed.

The following examples are presented to illustrate but not to restrict the present invention. Parts and percentages are by weight unless otherwise noted. The following abbreviation and definition are used in the Examples:

TTP=the reaction product of $PC_{l3}$ and commercially available m,p-cresol which contains minor amounts of related phenols.

$$\text{Conversion} = \frac{\text{mols of 3- and 4-PN's consumed}}{\text{mols of 3- and 4-PN's fed}} \times 100$$

EXAMPLES

Continuous single stage pentenenitrile hydrocyanations were run as described below:

A crimp-baffled round bottomed glass reaction vessel of about 25 cc reaction volume was used as the hydrocyanation reactor. All reagents entered the reaction vessel through sidearms fitted with rubber septa. The vessel was fitted with an overflow arm through which product flowed by gravity to a product receiver. It was also fitted with a mechanical stirrer and vigorous agitation was maintained. A small nitrogen purge was constantly applied. The vessel was heated by a heater-blower. The temperature of the reactor was thermocouple controlled by an electronic controller which regulated the reactor temperature by controlling the current in the blower heating element.

At start-up the vessel was charged with the expected product composition and brought to operating temperature. Then three electronically controlled syringe pumps fitted with 18 gauge needles several feet long were used to feed the reaction vessel. One syringe pump contained catalyst solution prepared as described in Shook et al. U.S. Pat. No. 3,903,120, one contained a mixture of refined pentenenitriles (PN's) and hydrogen cyanide, and one pump contained a 10 percent solution of $ZnCl_2$ in pentenenitriles. The syringe needles entered the vessel through the rubber septa referred to earlier and were submerged in the reaction liquid. The pump volumetric flow rates were controlled so as to maintain the conditions shown in the Table. Reactor effluent entered product bottles which were removed periodically as required for chemical analyses.

The 3- and 4-pentenenitrile (3,4-PN) conversion was controlled by the amount of HCN fed relative to the total 3,4-PN fed (PN's /HCN feed pump, catalyst/PN's feed pump and $ZnCl_2$/ PN's feed pump).

The unreacted HCN in the reactor (HCN leakage) was measured by periodically removing 0.05 ml reactor samples which were introduced into a 0.2 mm $CaF_2$ infrared cavity cell. An infrared spectrophotometer was then used to measure the cell HCN concentration using the HCN peak at ca.2085 $cm^{-1}$. In general, a run was considered a steady state run if 10 vessel turnovers with steady HCN leakage could be reached.

All of the examples in the Table were run at 50° C. It should be noted that three times less $ZnCl_2$ was used in Examples 1-3 than in the Comparative where the promoter was triphenylborane (TPB) rather than $ZnCl_2$. Moreover, after examples 1, 2 and 3 achieved steady state operation, TPB was substituted for $ZnCl_2$ at the same HCN/promoter ratio. In all three examples the HCN leakage rose sharply and steady state could not be maintained.

The Comparative Example—designated C in the Table—illustrates the use of TPB in steady state operation at the same HCN feed rate as in the examples but using three times the amount of promoter. When an attempt was made to run the Comparative at a feed ratio of HCN/TPB of about 200/1 rather than about 100/1 the HCN leakage rose rapidly to unacceptably high levels, indicating loss of reaction vitality. Even when attempts were made to run the Comparative at an HCN/TPB feed ratio of about 200/1 but at one quarter the rates shown in the Table reaction vitality could not be sustained. Over the region of feed TTP/Ni(0) ratio of from 5.45/1 to 8.13/1 the promoter $ZnCl_2$ was much more active than the promoter TPB.

TABLE

| Example No. | Feed Mol Ratio of HCN To | | | | Feed wt % Ni(O) | Conv. (%) | Overall Rate g ADN/cc/ min × 10$^4$) | Overall Rate g HCN/cc/ min × 10$^4$) | Cat Efficiency** | Mol Ratio of TTP to Ni(O) |
|---|---|---|---|---|---|---|---|---|---|---|
| | Ni(O) | Zn | TTP | 3,4-PN | | | | | | |
| 1 | 50.7 | 314.5 | 9.29 | 0.502 | 0.493 | 50.6 | 9.3 | 2.9 | 250 | 5.45 |
| 2 | 49.7 | 307.6 | 7.06 | 0.498 | 0.474 | 50.0 | 9.3 | 2.9 | 280 | 7.05 |
| 3 | 49.8 | 310.4 | 6.13 | 0.498 | 0.458 | 49.3 | 9.2 | 2.9 | 310 | 8.13 |
| 4 | 19.0 | 392.2 | 3.13 | 0.445 | 0.870 | 43.6 | 7.0 | 2.2 | 490 | 6.07 |
| 5* | 29.0 | 599.7 | 4.78 | 0.681 | 0.836 | 67.9 | 5.5 | 1.7 | 490 | 6.07 |
| C | 50.2 | 97.2$^1$ | 6.73 | 0.483 | 0.453 | 50.3 | 11.1 | 2.9 | 350 | 7.46 |

$^1$Triphenylborane, not ZnCl$_2$
*Example 5 is a two stage run in which 65.4% of the hydrogen cyanide was fed to the first stage and 34.6% was fed to the second stage.
**Mol Ratio of dinitriles made to moles of NI(O) consumed.

I claim:

1. A continuous process for the hydrocyanation of non-conjugated, ethylenically unsaturated organic nitriles having 5 carbon atoms to produce adiponitrile which process comprises continuously feeding the unsaturated nitriles, hydrogen cyanide, a zero-valent nickel ligand-containing catalyst having the general formula NiL$_4$ where L is P(OAr)$_3$ and Ar is an aryl or substituted aryl group having up to 18 carbon atoms and zinc chloride promoter, into a reaction vessel maintained at a temperature above about 25° C. but less than about 75° C., controlling the amount of hydrogen cyanide relative to other compounds participating in the reaction such that the overall feed mol ratio of hydrogen cyanide to unsaturated nitrile is in the range of about 0.35/1 to 0.8/1, the overall feed mol ratio of hydrogen cyanide to zero-valent nickel catalyst in the range of about 10/1 to 116/1 and the overall feed mol ratio of hydrogen cyanide to promoter in the range about 30/1 to 800/1 and the molar ratio of total ligand to zero-valent nickel introduced as a catalyst in the range of about 5.4 to 8.2, and continuously withdrawing from the reaction vessel a mixture containing adiponitrile.

2. The process of claim 1 in which the non-conjugated, ethylenically unsaturated organic nitrile is selected from the class consisting of 3-pentenenitrile, 4-pentenenitrile and mixtures thereof.

3. The process of claim 2 in which the Ar is selected from the class consisting of meta-tolyl, para-tolyl and mixtures thereof.

4. The process of claim 1 in which the temperature is maintained in the range of 30° to 65° C.

* * * * *